United States Patent
Ikeda et al.

(10) Patent No.: US 7,473,549 B2
(45) Date of Patent: Jan. 6, 2009

(54) TARGET RECOGNITION ELEMENT AND BIOSENSOR INCLUDING THE SAME

(75) Inventors: Atsushi Ikeda, Ikoma (JP); Jun-ichi Kikuchi, Souraku-gun (JP); Haruo Kotani, Takatsuki (JP); Yoko Hayashi, Kyoto (JP); Takaaki Shimasaki, Kyoto (JP)

(73) Assignee: Rohm Co., Ltd., Kyoto-shi (JP)

( * ) Notice: Subject to any disclaimer, the term of this patent is extended or adjusted under 35 U.S.C. 154(b) by 462 days.

(21) Appl. No.: 10/544,875

(22) PCT Filed: Feb. 5, 2004

(86) PCT No.: PCT/JP2004/001228

§ 371 (c)(1),
(2), (4) Date: Aug. 9, 2005

(87) PCT Pub. No.: WO2004/070372

PCT Pub. Date: Aug. 19, 2004

(65) Prior Publication Data

US 2006/0183124 A1  Aug. 17, 2006

(30) Foreign Application Priority Data

Feb. 10, 2003   (JP) .............................. 2003-032106

(51) Int. Cl.
*C12M 1/00* (2006.01)
*G01N 33/53* (2006.01)
*G01N 33/551* (2006.01)
*G01N 33/536* (2006.01)
*G01N 33/532* (2006.01)

(52) U.S. Cl. .................. 435/287.2; 435/7.1; 435/7.92; 436/524; 436/544; 436/536; 568/717

(58) Field of Classification Search ............... 435/7.1, 435/7.92, 287.2; 436/536, 544; 568/717
See application file for complete search history.

(56) References Cited

U.S. PATENT DOCUMENTS 6,238,930 B1 * 5/2001 Spichiger-Keller et al. .. 436/518

(Continued)

FOREIGN PATENT DOCUMENTS

JP 2002-94146 A 3/2002

(Continued)

OTHER PUBLICATIONS

Bianco et al. Molecular recognition by a silica-bound Fullerene derivative. 1997, J. Am. Chem. Soc. vol. 119, pp. 7550-7554.*

(Continued)

*Primary Examiner*—Long V Le
*Assistant Examiner*—Shafiqul Haq
(74) *Attorney, Agent, or Firm*—Global IP Counselors, LLP

(57) ABSTRACT

The present invention provides a target recognizing element wherein a receptor is fixed to an inclusion complex containing a mediator. The target recognizing element includes a first host molecule having hydrophilic groups and an inclusion site, a second host molecule having hydrophilic groups and an inclusion site, a receptor which is bonded to the hydrophilic groups of the second host molecule and which reacts with the target, and a guest molecule which is included by the inclusion site of the first host molecule and the inclusion site of the second host molecule and which transfers an electric charge generated by the reaction between the target and the receptor.

6 Claims, 7 Drawing Sheets

U.S. PATENT DOCUMENTS 6,652,833 B2 * 11/2003 Pines et al. .................. 424/9.3
2002/0131900 A1 9/2002 Jensen

FOREIGN PATENT DOCUMENTS

| JP | 2003-31832 A | 1/2003 |
|---|---|---|
| JP | 2004-22424 A | 1/2004 |
| WO | WO-01-96292 A1 | 12/2001 |

OTHER PUBLICATIONS

Patolsky et al., C60-mediated bioeletrocatalyzed oxidation of glucose with glucose oxidase, Journal of Electroanalytical Chemistry 454 (1998) 9-13.

Chen et al., Fullerene Self-Assembly onto (MeO)3Si(CH2)3NH2-Modified Oxide Surfaces, J. Am. Chem. Soc. 1993, 115, 1193-1194.

* cited by examiner

TARGET RECOGNITION ELEMENT AND BIOSENSOR INCLUDING THE SAME

TECHNICAL FIELD

The present invention relates to a target recognizing element which specifically bonds to a substance to be measured and to a biosensor which uses this target recognizing element.

BACKGROUND ART

Biosensors include enzyme sensors, immunosensors, and bacteriological sensors, and are considered to be very important for measuring material properties or substances (hereinafter referred to as targets) in a wide variety of fields such as the fields of medicine, food, and industry.

For instance, a glucose sensor measures the blood sugar level from the concentration of glucose in the blood. The glucose sensor has an electrode and an enzyme membrane which covers the electrode. Glucose oxidase (GOD) is fixed on the enzyme membrane as a receptor which specifically reacts with glucose.

Glucose is oxidized by GOD in the glucose sensor according to the reaction formula (1), and is broken down into gluconic acid and hydrogen peroxide.

(Formula 1)

$$C_6H_{12}O_6 + O_2 \rightarrow C_6H_{10}O_6 + H_2O_2 \qquad (1)$$

Next, the hydrogen peroxide produced in the reaction formula (1) is diffused in the solution between the electrode and the enzyme membrane to the electrode surface, and undergoes electrolysis at the electrode as shown in reaction formula (2), and the electrons are transferred to the electrode.

(Formula 2)

$$H_2O_2 \rightarrow *2H^+ + O_2 + 2e^- \qquad (2)$$

A proportional relationship exists between the glucose concentration, the diffusion of glucose to the enzyme membrane, and the diffusion of hydrogen peroxide in the solution, and the glucose concentration can be obtained by measuring the electrical current from the electrolysis reaction of reaction formula (2). However, with this type of glucose sensor, the transfer of electrons to the electrode from the enzyme membrane is dependent on the diffusion speed and the diffusion concentration or the like of the hydrogen peroxide to the electrode, so rapid measurements and measurements with high electrical currents are difficult.

Therefore, biosensors are being developed which transfer a charge between a receptor and the electrode using a mediator. FIG. 7 shows the operating principle of a mediator type biosensor, and the following reaction takes place between the mediator M, an enzyme E, and a substrate S which reacts with the enzyme E.

Electrons are transferred by the oxidation reduction reaction between the oxidized enzyme $E_{ox}$ and the substrate S, and reduced enzyme $E_{red}$ and product P are produced. Next, oxidized enzyme $E_{ox}$ and reduced mediator $M_{red}$ are produced by the oxidation reduction reaction between the reduced enzyme $E_{red}$ and the oxidized mediator $M_{ox}$. Finally, oxidized mediator $M_{ox}$ is produced and electrons are transferred to the electrode by the oxidation reduction reaction between reduced mediator $M_{red}$ and the electrode. In other words, the electrons generated by the enzyme reaction are rapidly transferred in high-volume from the enzyme to the electrode through the mediator. At this time, oxidation and reduction is repeatedly occurring between the enzyme E and the mediator M. The aforementioned enzyme reaction was for the case where the substrate S is oxidized and electrons are transferred to the electrode, but if the substrate S is reduced and electrons are consumed, the electrons will transfer to the enzyme from the electrode by the reverse cycle.

FIG. 8 shows the structure of a mediator type biosensor with an electrode which uses $C_{60}$ fullerene as shown in the Journal of Electroanalytical Chemistry 454, 9-13, 1998. The $C_{60}$ fullerene 2, which is the mediator, is fixed to the electrode 1 by a self organizing monomolecular film 3 made from -HS—$(CH_2)_2$—$NH_2$. The surface of the $C_{60}$ fullerene 2 is modified with =CH—COOH in order for the $C_{60}$ fullerene 2 and the self organizing monomolecular film 3 to bond. Furthermore, the enzyme 4 and the $C_{60}$ fullerene are not bonded, and the enzyme 4 is suspended in the solution.

With the biosensor described in the aforementioned documentation, electrons are generated by the oxidation reduction reaction between the glucose, which is the substrate 5, and the GOD, which is the enzyme 4, and the electrons are transferred to the electrode 1 through the $C_{60}$ fullerene 2, and the glucose concentration is measured.

The mediator type biosensor shown in the aforementioned documentation uses $C_{60}$ fullerene 2, which has excellent properties for electron attracting and electron donating. However, the enzyme 4 is suspended in the solution and is not bonded with the $C_{60}$ fullerene 2. Therefore, even when electrons are transferred by the oxidation reduction reaction between the enzyme 4 and the substrate 5, if the enzyme 4 and the $C_{60}$ fullerene 2 are not bonded, the $C_{60}$ fullerene 2 cannot transfer a large volume of electrons at high-speed from the enzyme 4 to the electrode 1.

Furthermore, modifying groups are required on the surface of the $C_{60}$ fullerene 2 in order to fix the $C_{60}$ fullerene 2 to the electrode 1. Therefore, the electron distribution of the Π bonds, which contribute to the transmission of electricity, will be inconsistent, and there will be problems with a loss of the properties of $C_{60}$ fullerene 2, including electron attracting and electron donating.

Therefore, an object of the present invention is to provide a target recognizing element wherein a receptor is fixed to an inclusion complex which includes a mediator.

Furthermore, another object of the present invention is to provide a biosensor wherein the position of the mediator is fixed with regard to the electrode without using modifying groups on the surface of the mediator.

SUMMARY OF THE INVENTION

In order to resolve the aforementioned problems, the first aspect of the present invention provides a target recognizing element comprising a first host molecule having a hydrophilic group and an inclusion site, a second host molecule having hydrophilic groups and an inclusion site, a receptor which is bonded to the hydrophilic groups of the second host molecule and which reacts with the target, and a guest molecule which is included in the inclusion site of the first host molecule and in the inclusion site of the second host molecule, and which transmits a charge produced by the reaction between the target and the receptor.

The second host molecule and receptor are bonded together and the receptor is fixed, so the reaction between the receptor and target can always be performed close to the guest molecule which is included by the first host molecule and the second host molecule. Therefore, the electric charge generated by this reaction can be transferred in large volume and at high-speed by the guest molecule. Furthermore, the first and second host molecules have hydrophilic groups, so even if the guest molecule is insoluble, the target recognizing element can be used in solution, and for instance, the target recognizing element can easily be arranged on a substrate.

The second aspect of the present invention provides the target recognizing element according to the first aspect wherein the first host molecule is a first calixarene, the second host molecule is a second calixarene, and the guest molecule is fullerene.

The inclusion sites of the first and second calixarenes include the fullerene by hydrophobic interaction and by Π-Π interaction, so the insoluble fullerene which is the mediator can be made water-soluble without using special modifying groups. Therefore, the distribution of Π electrons which contribute to electric transmission will remain consistent, and therefore the properties of fullerene, which has low ionization energy and high electron affinity, will not be lost. Therefore, the electric charge can be transferred in high-volume at high-speed by the fullerene.

The third aspect of the present invention provides the target recognizing element according to the first aspect, wherein the receptor is one or a combination of a plurality of substances selected from a group including enzymes, antibodies, DNA (deoxyribonucleic acid), and peptides.

Biological materials can be specifically captured using enzymes, antibodies, DNA, or peptides.

The fourth aspect of the present invention provides the target recognizing element according to the first or second aspect, further comprising at least one layer of a polymer film between the second host molecule and the receptor.

The polymer film flattens the bonding interface between the second host molecule and the receptor without damaging the three-dimensional structure of the receptor, so loss of receptor activity can be prevented. Furthermore, the bonding area can be increased, so the bond between the second host molecule and the receptor can be made stronger.

The fifth aspect of the present invention provides the target recognizing element according to be fourth aspect wherein the polymer film comprises a poly(diallyl dimethyl ammonium chloride) layer and a polyvinyl potassium sulfate layer.

The sixth aspect of the present invention provides the target recognizing element according to the first aspect, and further comprises a polyion complex film which covers the receptor.

The bond between the receptor and the second host molecule can be strengthened by the polyion complex film, so the durability of the target recognizing element can be increased.

The seventh aspect of the present invention provides the target recognizing element according to the first aspect wherein the receptor is bonded to the hydrophilic groups of the second host molecule under conditions where the pH is between 4 and 8, and the temperature is between 15 and 45° C.

Loss of receptor activity can be prevented by bonding the receptor and the second host molecule under the aforementioned conditions.

The eighth aspect of the present invention provides a biosensor comprising a first host molecule having hydrophilic groups and an inclusion site, a second host molecule having hydrophilic groups and an inclusion site, an electrode to which the hydrophilic groups of the first host molecule are bonded, a receptor which is bonded to the hydrophilic groups of the second host molecule and which reacts with the target, and a guest molecule which is included in the inclusion site of the first host molecule and in the inclusion site of the second host molecule, and which transmits a charge produced by the reaction between the target and the receptor to an electrode.

The receptor is fixed to the second host molecule, so the reaction between the receptor and the target can always be performed close to the guest molecule. Therefore, the electric charge generated by this reaction can be transferred in high-volume and at high-speed from the receptor to the electrode by the guest molecule. Furthermore, the guest molecule is included by the first and second host molecules and is securely fixed to the electrode, so modifying groups for fixing the guest molecule to the electrode are not required on the guest molecule. Therefore, the property of the guest molecule for transferring a high quantity of electrical charge at high-speed will not be lost. Furthermore, the first and second host molecules have hydrophilic groups, so even if the guest molecule is insoluble, the biosensor can easily be used in a solution.

The ninth aspect of the present invention provides the biosensor according to the eighth aspect further comprising detecting means connected to the electrode.

The charge which is transferred to the electrode can be measured by the detecting means.

The tenth aspect of the present invention provides the biosensor of the eighth aspect, wherein the first host molecule is the first calixarene, the second host molecule is the second calixarene, and the guest molecule is fullerene. The effect is similar to that of the second aspect.

The eleventh aspect of the present invention provides the biosensor of the eighth aspect, wherein the receptor is one or a combination of a plurality of substances selected from a group including enzymes, antibodies, DNA, and peptides. The effect is similar to that of the third aspect.

The twelfth aspect of the present invention provides the biosensor according to any one of the eighth through tenth aspects, further comprising at least one layer of a polymer film between the second host molecule and the receptor. The effect is similar to that of the fourth aspect.

A thirteenth aspect of the present invention provides the biosensor of the twelfth aspect, wherein the polymer film is comprising a poly(diallyl dimethyl ammonium chloride) layer and a polyvinyl potassium sulfate layer. The effect is similar to that of the fifth aspect.

The fourteenth aspect of the present invention provides the biosensor of the eighth aspect, further comprising a polyion complex film which covers the receptor. The effect is similar to that of the sixth aspect.

The fifteenth aspect of the present invention provides the biosensor of the eighth aspect, wherein the receptor is bonded to the hydrophilic groups of the second host molecule under conditions in which the pH is between 4 and 8, and the temperature is between 15 and 45° C. The effect is similar to that of the seventh aspect.

The sixteenth aspect of the present invention provides detecting the electrical charge produced from the reaction between the target and the receptor using the biosensor according to the ninth aspect.

Using the biosensor of the ninth aspect, the electrical charge can be effectively detected.

The seventeenth aspect of the present invention provides the detection method according to the sixteenth aspect, wherein the guest molecule is fullerene, and an excitation step to photoexcite the fullerene is also included.

The fullerene is photoexcited by radiating the fullerene with light, so the high electron affinity, low ionization energy properties of the fullerene can be increased. Therefore, the reaction speed and the reaction sensitivity of the biosensor can be increased.

The eighteenth aspect of the present invention is a manufacturing method for the biosensor according to the eight aspect, comprising an inclusion complex producing step of combining and mixing a solution containing the first host molecule and the second host molecule with a solution containing the guest molecule to produce an inclusion complex comprising the first host molecule, the second host molecule, and the guest molecule; an electrode forming step of bonding an anionic or a cationic molecule to the surface of an electrode; an inclusion complex bonding step of bonding the electrode formed in the electrode forming step with the hydrophilic groups of the first host molecule in the inclusion complex; and a receptor bonding step of bonding the receptor and the hydrophilic groups on the second host molecule in the inclusion complex; wherein the guest molecule is included by the inclusion site of the first host molecule and the inclusion site of the second host molecule in the inclusion complex produced in the inclusion complex producing step. A biosensor can be produced which has the same effect as the eighth aspect.

The nineteenth aspect of the present invention provides the biosensor manufacturing method of the eighteenth invention, wherein the hydrophilic group of the second host molecule and the receptor are bonded together under conditions where the pH is between 4 and 8, and the temperature is between 15 and 45° C. in the receptor bonding step. The effect is similar to that of the seventh aspect.

PREFERRED EMBODIMENTS OF THE INVENTION

Basic Structure

Figure 1A:
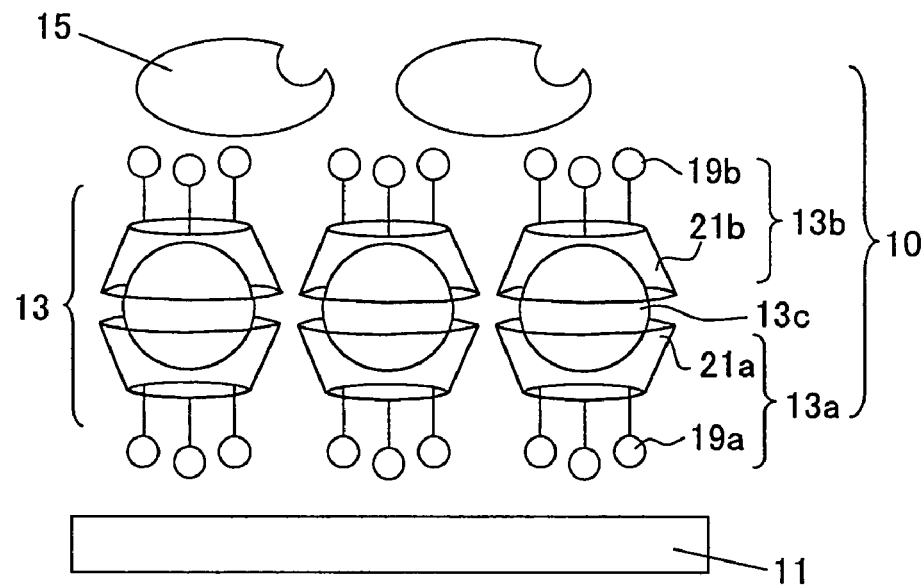
FIG. 1(a) is a diagram showing the basic structure of an electrode for the mediator type biosensor of the present invention.

FIG. 1(a) shows the basic structure of the electrode of the mediator type biosensor of the present invention. The mediator type biosensor has an electrode 11 and a target recognizing element 10 which is fixed on the electrode 11. The target recognizing element 10 has an inclusion complex 13 and a receptor 15 fixed on the inclusion complex 13. The inclusion complex 13 has a first host molecule 13a, a second host molecule 13b, and a guest molecule 13c. The first guest molecule 13a has hydrophilic groups 19a and an inclusion site 21a, and similarly, the second host molecule 13b also has hydrophilic groups 19b and an inclusion site 21b. The inclusion complex 13 has a structure such that the guest molecule 13c is included by the inclusion site 21a of the first guest molecule 13a and the inclusion site 21b of the second host molecule 13b, and in whole is surrounded by the hydrophilic groups 19a and 19b. The included guest molecule 13c functions as a mediator which transfers an electric charge from the receptors 15 to the electrode 11. For instance, fullerene may be suggested for the guest molecule 13c and calixarene as the first and second host molecules 13a, 13b. Furthermore, the first and second host molecules 13a, 13b may also be different substances. Note, if the first and second host molecules 13a, 13b are the same substance, creating the inclusion complex 13 will be simplified, which is preferable. For instance, if two types of substances A, B are used as the first and second host molecules 13a, 13b to produce the inclusion complex 13, three types of complexes will be generated during preparation (AA, AB, BB). Therefore, these complexes will need to be separated, and producing the inclusion complex 13 will become difficult. On the other hand, if the same substance is used, separation will not be necessary so production will be simplified. Furthermore, if the substances are the same, identifying the substance of the first host molecule 13a on the electrode 11 side and the substance of the second host molecule 13b on the side opposite to the electrode 11 will not be necessary, and the control of fixing the inclusion complex will be simplified.

The electrode 11 is ionic bonded by the electrostatic interaction of the hydrophilic groups 19a of the first host molecule 13a. The bond between the electrode 11 and the inclusion complex 13 is not restricted to ionic bonds, and various other bonds such as covalent bonds and coordinate bonds can be conceived. The electrode 11 may be any inert electrode, and electrodes of Au, Ag, Pt, ITO, and carbon or the like may be used. The use of carbon is preferable because carbon is inexpensive, can easily be formed, and provides a relatively stable electrode.

The receptor 15 is fixed to the inclusion complex 13 by the hydrophilic groups 19b of the second host molecule 13b. The bond between the receptor 15 and the hydrophilic groups 19b is formed by ionic bonds or covalent bonds, or the like. If the receptor 15 is one of an enzyme, antibody, DNA, cell, or peptide, or a combination thereof, biological substances can specifically be captured, and is therefore preferable.

Figure 1B:
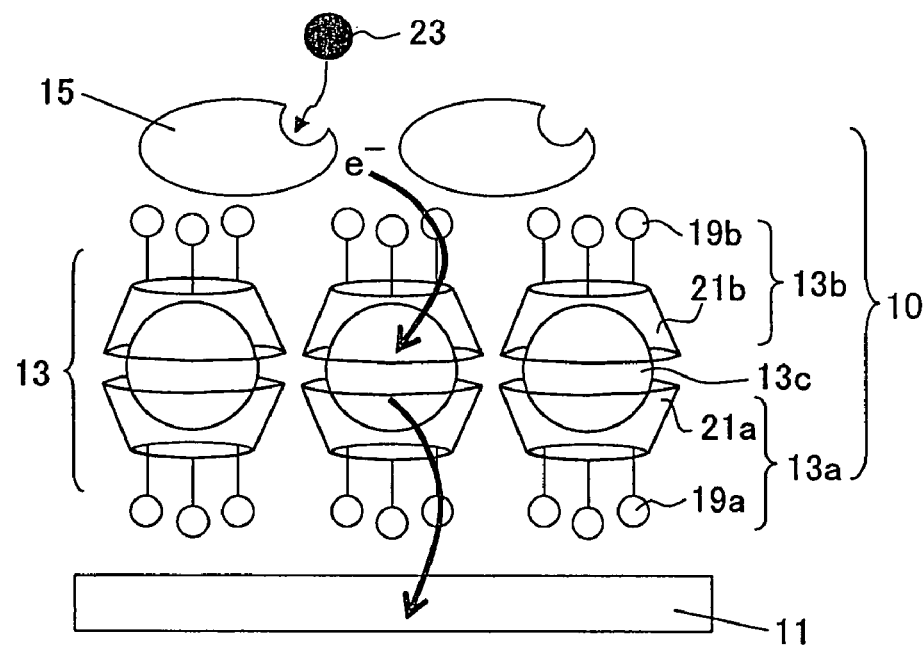
FIG. 1(b) is an explanatory diagram which describes the operation of the biosensor of (a).

FIG. 1(b) is a schematic diagram which describes the function of the biosensor of FIG. 1(a). The target 23 is a substance which is captured by the receptor 15. This biosensor functions as shown below. The target 23 is captured by the receptor 15, and an oxidation reduction reaction occurs between the target 23 and the receptor 15. Electrons $e^-$ are generated by this oxidation reduction reaction, and for instance, the generated electrons $e^-$ are transferred to the electrode 11 by the guest molecule which is included by the first and second host molecules 13a, 13b. The presence and quantity or the like of the target 23 can be measured by measuring the change in the electrical charge of the electrode 11. In FIG. 1(b), the case where a negative charge is transferred is described, but a positive charge may also be transferred.

With this type of biosensor, the receptor 15 is fixed to the inclusion complex 13 by the bond between the second host molecule 13b and the receptor 15. Therefore, the reaction between the receptor 15 and the target 23 can always be performed in close proximity to the guest molecule 13c which is included by the first host molecule 13a and the second host molecule 13b. Therefore, the electrical charge produced by this reaction can be transferred in high quantities and at high-speed from the receptor 15 to the electrode 11 by the guest molecule 13c. Furthermore, the first and second host molecules 13a, 13b have hydrophilic groups 19a, 19b, so even if the guest molecule 13c is insoluble, the guest molecule 13c can be used in the solution where the target 23 is measured.

Furthermore, the target recognizing element 10 can easily be arranged on a board or the like.

FIRST EMBODIMENT

Figure 2:
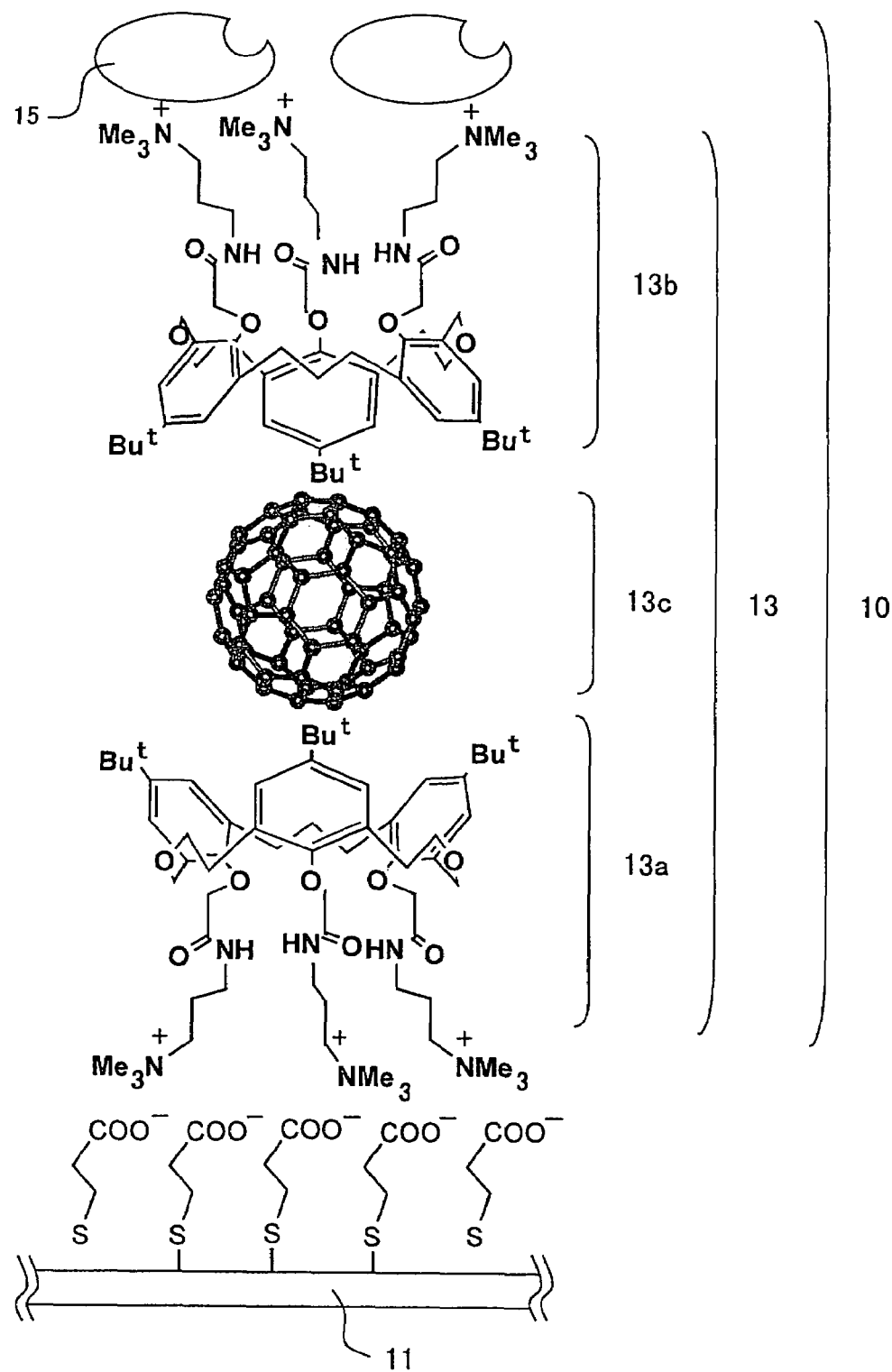
FIG. 2 shows the structure of the biosensor according to a first embodiment.

FIG. 2 shows the structure of a biosensor according to a first embodiment. The biosensor of the first embodiment will be described below while referring to FIG. 1 and FIG. 2.

Structure of Biosensor

With the biosensor of the first embodiment, the target recognizing element 10 wherein a receptor 15 is fixed to an inclusion complex 13 is fixed to the electrode 11. In this case, the guest molecule 13c is $C_{60}$ fullerene, and the first and second host molecules 13a, 13b include calix[3]arene. Calix[3]arene is a structure with three phenol derivatives connected in a ring at the meta position, the oxygen atoms side of the phenol component is structured to be hydrophilic, and the $C_{60}$ fullerene is included at the inclusion site on the benzene ring side which is opposite to the phenol component. Therefore, the inclusion site is structured to be hydrophobic. The hydrophilic groups of the calix[3]arene shown in FIG. 2 are modified using cationic quaternary amines and have a positive electrical charge. Furthermore, the electrode 11 is a metal and is modified by anionic carboxylic acid, and has a negative charge. Therefore, the electrode 11 and the hydrophilic groups of the calix[3]arene are bonded by electrostatic interaction. The receptor 15 for instance is a lactate dehydrogenase, which is an enzyme which reacts with pyruvic acid in the blood as the target. The lactate dehydrogenase, which has an acidic isoelectric point, has a negative electrical charge in a neutral aqueous solution, and is bonded to the hydrophilic groups of the calix[3]arene by electrostatic interaction.

In the above case, the charge on the hydrophilic groups of the calix[3]arene was positive, and the charge on the surface of the enzyme and the surface of the electrode 11 was negative, but it is also acceptable for the charge on the hydrophilic groups of the calix[3]arene to be negative and the charge on the surface of the enzyme or the surface of the electrode 11 to be positive. Furthermore, the bond between the receptor 15 and the inclusion complex 13 and the bond between the inclusion complex 13 and the electrode 11 may be a bond other than electrostatic interaction, such as a covalent bond.

The guest molecule 13c, which is the mediator, may be a substance other than $C_{60}$ fullerene, and for instance higher-order fullerenes such as $C_{70}$, $C_{76}$, $C_{78}$, $C_{82}$, $C_{84}$, $C_{86}$, $C_{88}$, $C_{90}$, $C_{92}$, $C_{94}$, or $C_{96}$ are acceptable. Furthermore, if the fullerene includes a La atom, electrons will be provided from the included element to the fullerene and the fullerene will have surplus electrons, so not only will the fullerene have increased electrical conductivity, but the initial response time will be shorter, which is preferable.

Furthermore, in FIG. 2, the first and second host molecules 13a, 13b are both identical calix[3]arene, but it is also acceptable to use different calixarene such as using calix[4]arene for the first host molecule 13a and calix[3]arene for the second host molecule 13b. Note, if the same calixarene is used, the inclusion complex 13 will be easier to produce as described above, and therefore this is preferable.

In the preceding example, the enzyme lactate dehydrogenase was used as the receptor 15 in order to detect pyruvic acid, but other enzymes may be used depending on the target to be detected. Other enzymes which may be used include for instance, oxidases (such as glucose oxidase), dehydrogenases (such as alcohol dehydrogenase), reductases (such as adrenodoxin), oxygenases, hydroperoxygenases (such as catalase), urease, creatinine deaminase, or the like. If urease is used as the enzyme, blood urea nitrogen (BUN) can be measured, and if creatinine deaminase is used, then creatinine can be measured, and thus kidney disease can be diagnosed.

With the aforementioned biosensor, the $C_{60}$ fullerene is included by the $\Pi$-$\Pi$ interaction and the hydrophobic interaction of the inclusion sites of the calix[3]arene, which is the first and second host molecule 13a, 13b, and thus stably fixed to the electrode 11. At this time, the $C_{60}$ fullerene is included by the calix[3]arene in the suspended state, and modifiers are not bonded. Therefore, the distribution of $\Pi$ electrons which contribute to electrical conductivity will remain consistent, so the high electron affinity and low ionization energy properties of fullerene will not be lost. Therefore, a large electric charge can rapidly be transferred from the receptor to the $C_{60}$ fullerene and the electrode. Furthermore, the side opposite to the inclusion site of the calix[3]arene is constructed with hydrophilic phenol, so water insoluble $C_{60}$ fullerene can be made soluble without using modifying groups by the inclusion of the $C_{60}$ fullerene in the calix[3]arene. Therefore, the biosensor can easily be used in a solution.

Detection Method Using Biosensor

Figure 3A:
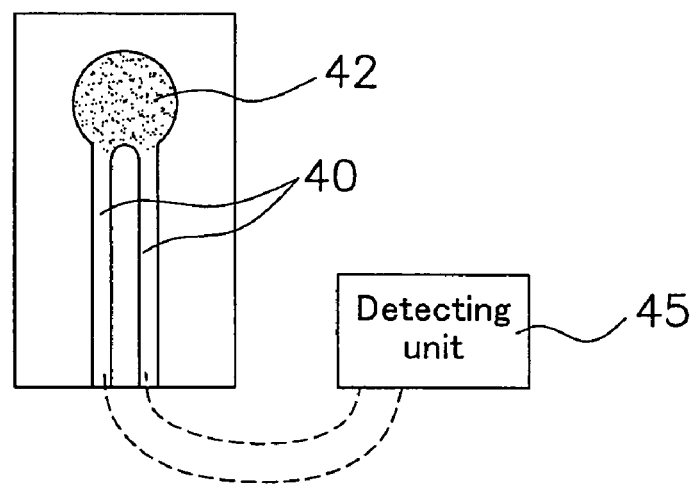
FIG. 3(a) is an example (1) of a biosensor with a detection unit. (b) is an example (2) of a biosensor with a detection unit.

FIG. 3(a), (b) show an example of the biosensor with a detecting unit. In FIG. 3(a), the target recognizing element 42 from FIG. 2 is fixed to an electrode 40, and the electrode 40 is connected to a detecting unit 45. A test sample is dripped onto the region of the electrode 40 where the target recognizing element 42 is fixed, the current is measured by the detecting unit 45, and the concentration or the like of the target in the test sample is calculated.

Figure 3B:
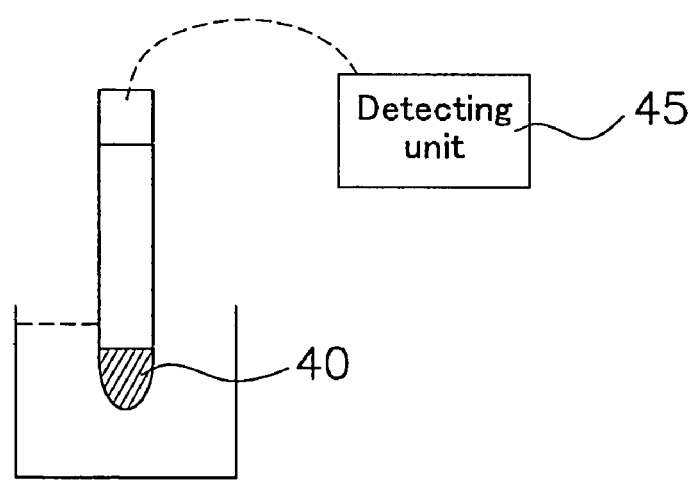

On the other hand, in FIG. 3(b), the tip of the electrode 40 to which the target recognizing element 42 has been fixed is immersed in the test solution, and the current is measured by the detecting unit 45.

Note, if external light is radiated on the target recognizing element 42 while measuring, the $C_{60}$ fullerene will be photo-excited, so the high electron affinity and low ionization energy properties of the fullerene can be increased. Therefore, the response speed of the target recognizing element will be faster, and the reaction sensitivity can be increased. The wavelength band where fullerene becomes photoexcited is broad, but in particular, excitation is more efficient at wavelengths at or below 620 nm. Red LED and Ar laser may be used as light sources which have this wavelength.

Biosensor Manufacturing Method

The biosensor of the first embodiment is manufactured as shown below. Calix[3]arene and $C_{60}$ fullerene are mixed in an aqueous solution and the mixture is agitated. Ultrasonic treatment is preferably used for the agitation. Because of this treatment, the $C_{60}$ fullerene will be included by the hydrophobic groups which are the inclusion site of the calix[3]arene, to produce an inclusion complex 13. The electrode 11 and the hydrophilic groups of the calix[3]arene are modified with anionic or cationic molecules. At this time, the bond between the electrode 11 and the calix[3]arene and the bond between the calix[3]arene and the lactate dehydrogenase are modified to bond by electrostatic interaction. The modified inclusion complex 13, electrode 11, and the lactate dehydrogenase are bonded together to obtain a biosensor which is capable of measuring pyruvate acid which is the target. At this time, if the bond between the lactate dehydrogenase and the inclusion complex 13 is formed under conditions where the pH is between 4 and 8 and the temperature is between 15 and 45° C., loss of enzymatic activity can be prevented, and therefore this is preferable.

EXPERIMENTAL EXAMPLE 1

A experimental example in which an inclusion complex was created by including $C_{60}$ fullerene in calix[3]arene, and lactate dehydrogenase was fixed to the inclusion complex as the receptor, is shown below.

(1) Synthesis of Calix[3]arene

First, using the triester derivatives of calix[3]arene as a raw material, an excess of N, N-dimethylpropane diamine was added to synthesize the precursor of the calix[3]arene using aminolysis. This precursor was N-methylated using dimethyl sulfate to synthesize calix[3]arene with quaternary amines on the end.

(2) Preparation of Calix[3]arene and $C_{60}$ Fullerene $C_{60}$ fullerene (72 mg, 0.1 mmol) was mixed into an aqueous solution of calix[3]arene (10 ml, 0.5 mmol/dm$^3$) synthesized as shown above, and after repeated agitation and ultrasonic treatment, the undissolved fullerene was removed by centrifugal separation, to prepare an aqueous solution of the inclusion complex which was the calix[3]arene and $C_{60}$ fullerene complex. The width of the inclusion complex produced was approximately 1 nm, and the height was approximately 2 nm.

(3) Preparation of the Electrode

On the other hand, an electrode 11 with anionic molecules on the surface was created by immersing the metal electrode in an ethanol solution containing sodium 2-mercaptoethane sulfonate.

(4) Fixing the Inclusion Complex

The inclusion complex is tightly arranged on the electrode by immersing the electrode prepared according to (3) above in an aqueous solution of inclusion complex (0.25 mmol/dm$^3$) in order to produce a biosensor. At this time, the inclusion complex was bonded to the electrode by electrostatic interaction.

(5) Fixing the Receptor

Next, the electrode with the inclusion complex was immersed for 20 minutes at room temperature in a HEPES (2-[4-(2-hydroxyethyl)-1-piperazinyl]ethanesulfonic acid) buffered solution (pH=7.0) containing lactate dehydrogenase (0.2 mg/ml), and the enzyme was fixed to the inclusion complex by electrostatic interaction.

Figure 6:
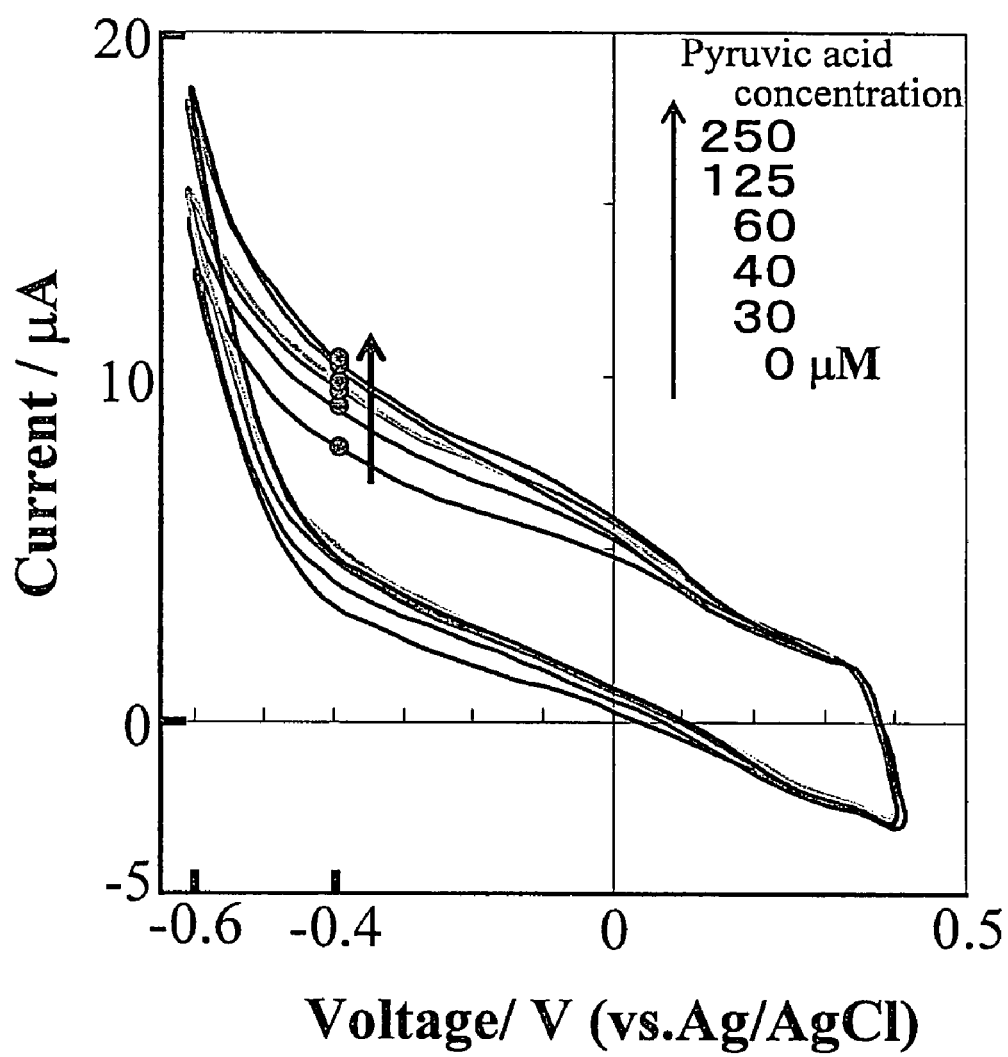
FIG. 6 shows the electrical characteristics of the biosensor according to the first embodiment.
Figure 7:
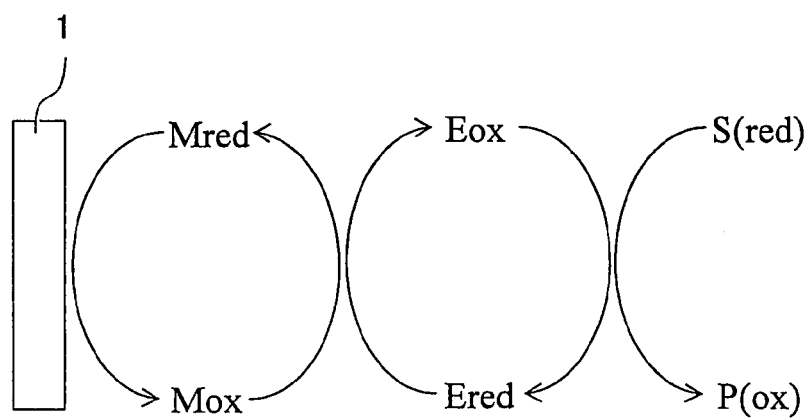
FIG. 7 is an explanatory diagram which describes the operating principles of a mediator type biosensor.
Figure 8:
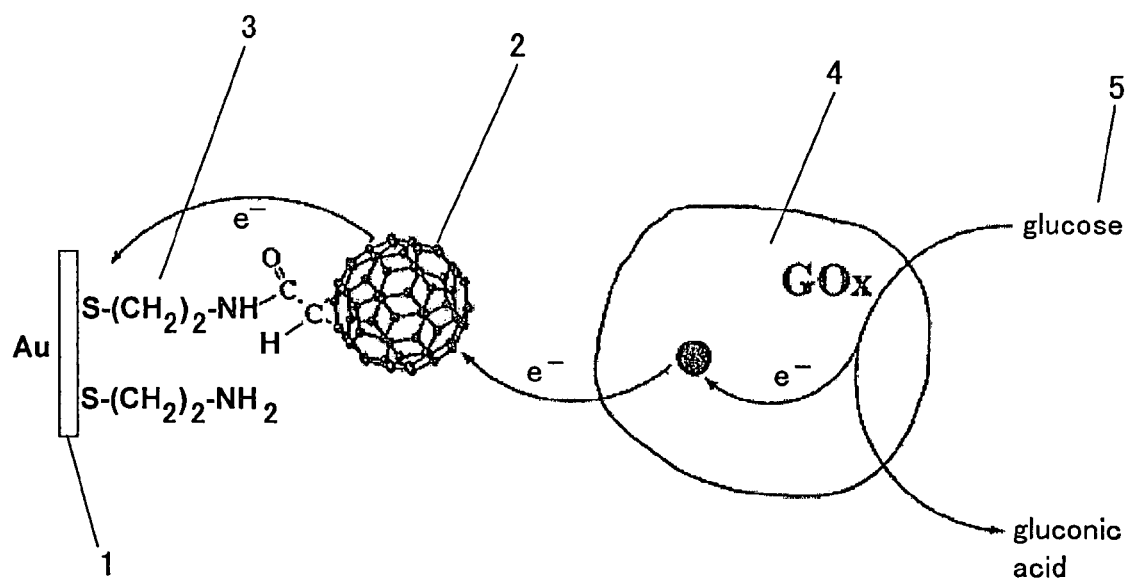
FIG. 8 shows the structure of the electrode unit of a conventional mediator type biosensor which uses $C_{60}$ fullerene.

The electrical characteristics obtained using the cyclic voltammetry measurement method of the biosensor of the first embodiment obtained by the aforementioned manufacturing method is shown in FIG. 6. This is the property diagram when a biosensor chip to which lactate dehydrogenase (LDH) was fixed is immersed in a solution of 125 μM of reduced nicotinamide adenine dinucleotide (NADH) and between 0 and 250 μM of pyruvic acid. A biosensor chip which is sensitive enough to measure minute quantities of pyruvic acid could be obtained.

SECOND EMBODIMENT

A biosensor with the structure shown in the first embodiment wherein the receptor 15 is an antibody, DNA, cell, or peptide will be described.

Antibody

If the receptor 15 is an antibody, the target will be antigens which specifically react with the receptor 15, and the existence and concentration or the like of the target can be measured. The types of antigen include viruses, bacteria, pollen, mold, and dust mites or the like. To illustrate, a case where the antibody is "Mouse IgG" and the antigen is "Protein A" will be described.

First, the antigen "Protein A" is injected into a mouse, and "Mouse IgG" antibody is produced using the immuno response of the mouse. The antibody "Mouse IgG" is extracted, purified, and fixed to the inclusion complex 13. The Fc region of the mouse IgG is modified with a carboxyl group or an amino group or the like in order to fix to the inclusion complex by electrostatic interaction or covalent bonding. When Protein A is injected therein, the Protein A and the Mouse IgG will specifically bond. The electric charge produced from the Protein A made from polar molecules will reach the electrode 11 through the antibody and the inclusion complex 13. The quantity of the antigen Protein A can be determined by measuring the current flowing to the electrode 11.

DNA

A method to detect target DNA, for a case where the receptor 15 is probe DNA which specifically reacts with the DNA that is the target, will be described.

DNA has a double helical structure, but when used as the receptor 15 for the biosensor, a single strand is used. First, a single strand DNA which has the base sequence and complementation as the target DNA is artificially organically synthesized to produce the probe DNA. This probe DNA is fixed on the inclusion complex 13. Next, the desired DNA is extracted and purified from a biological sample, and heated to 95° for instance to obtain a single strand. If this DNA and the base sequence of the probe DNA are complementary, or in other words if the DNA in the test sample has the base sequence of the DNA to be detected, both DNA will combine and form a double helix. The double helix structure will be specifically bonded, and an intercalator which is the source of the electrical charge is inserted in the gap in the double helical structure. Therefore, the presence of a double helical structure, or in other words, whether or not the DNA in the test sample has the target base sequence, can be determined by changes in the current flowing to the electrode 11.

Cells

The method for detecting an antigen, which is the target, when the receptor 15 is a cell will be described. Immunocyte such as NK cells or B cells are extracted and purified from an organism, and then fixed to the inclusion complex 13. If a protein molecule terminal group which is bonded to the cell surface is used to fix the cell to the inclusion complex 13, the fixing can be easily performed, and this is preferable. The antigen may be a virus, bacteria, pollen, mold, or dust mite or the like. When the biosensor to which the cell is fixed is introduced to the test sample, the cell which is the receptor 15 will attack the antigen and the antigen will be disintegrated by the enzymes in the cell. The electrical charge produced by the disintegration process will be transferred to the electrode 11 through the inclusion complex 13. The quantity of antigen can be determined by measuring the electrical current flowing to the electrode 11 at this time.

Peptides

The method for detecting a peptide, which is the target, when the receptor 15 is a peptide will be described. A probe peptide which specifically reacts with the desired target is created in a phage using genetic engineering methods. This peptide is extracted, purified, and fixed to the inclusion complex 13. When a biosensor which contains this inclusion complex 13 is injected into the test sample, the probe peptide and a peptide which corresponds to the charge of the side groups of the amino acids which make up the probe peptide, will bond together. At this time, the target peptide can be detected and quantified by measuring the electrical current flowing to the electrode 11.

THIRD EMBODIMENT

Figure 4A:
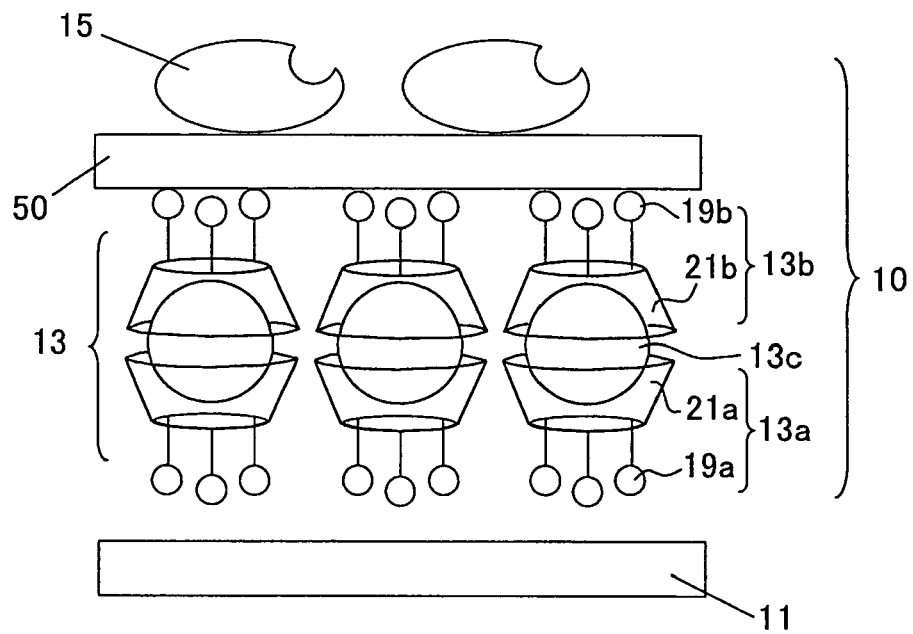
FIG. 4(a) shows a structure (1) of the biosensor according to a third embodiment. (b) shows a structure (2) of the biosensor according to the third embodiment.

FIGS. 4(a), (b) show the structure of the biosensor of the third embodiment. Flag numbers which are identical to those in FIG. 1 identify similar structural elements as those in the first embodiment. The biosensor of FIG. 4(a) comprises the target recognizing element 10 of FIG. 1 with a polymer film 50. The polymer film 50 is established between the second host molecule 13b and the receptor 15. This polymer film 50 flattens the contact interface between the second host molecule 13b and the receptor 15 without damaging the three-dimensional structure of the receptor 15, so a loss of activity of the receptor 15 can be prevented. Furthermore, the contact surface area can be increased, so the second host molecule 13b and the receptor 15 can be more tightly connected.

Figure 4B:
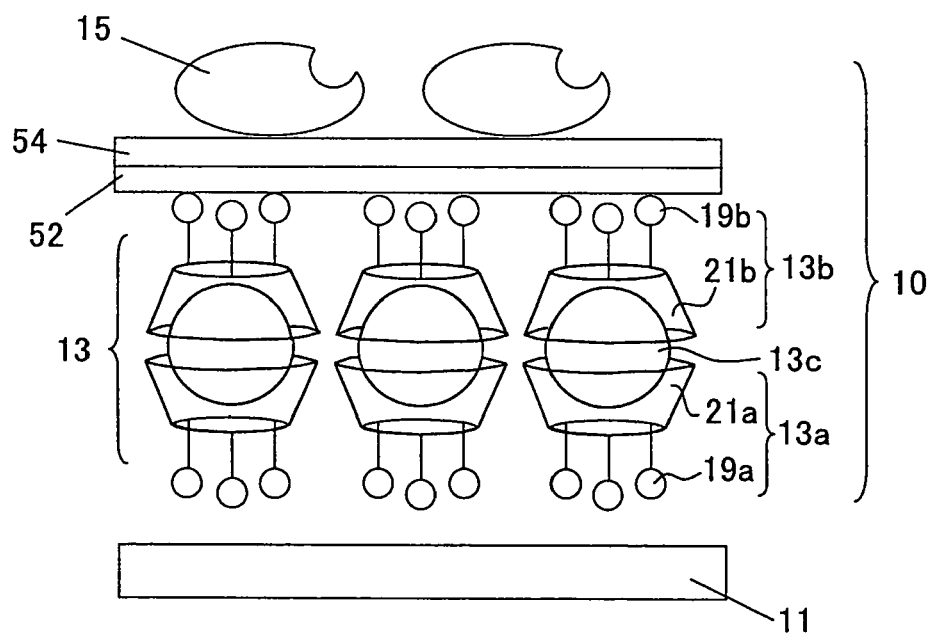

As shown in FIG. 4(b), the polymer film 50 may be a polymer film 52, 54 with a double layer structure. For example, PDDA (poly(diallyl dimethyl ammonium chloride)) 52 which is a cationic polymer film is formed on the inclusion complex 13, and PVS (polyvinyl potassium sulfate) 54 which is an anionic polymer film is formed thereon, thus fixing the enzyme to the inclusion complex 13. In this manner, the polymer film 50 will have an anionic and cationic double layer structure, so a positively charged enzyme can be fixed in place of the negatively charged enzyme. Furthermore, the polymer film 50 may also have two or more layers.

EXPERIMENTAL EXAMPLE 2

An experimental example in which an inclusion complex was created by including $C_{60}$ fullerene in calix[3]arene, and then a polymer film and lactate dehydrogenase as the receptor were fixed to the inclusion complex, is shown below.

(1) Synthesis of Calix[3]arene

First, using the triester derivatives of calix[3]arene as a raw material, an excess of N, N-dimethylpropane diamine was added to synthesize the precursor of the calix[3]arene using aminolysis. This precursor was N-methylated using dimethyl sulfate to synthesize calix[3]arene with quaternary amines on the end.

(2) Preparation of Calix[3]arene and $C_{60}$ Fullerene $C_{60}$ fullerene (72 mg, 0.1 mmol) was mixed into an aqueous solution of calix[3]arene (10 ml, 0.5 mmol/dm$^3$) synthesized as shown above, and after repeated agitation and ultrasonic treatment, the undissolved fullerene was removed by centrifugal separation, to prepare an aqueous solution of the inclusion complex which was the calix[3]arene and $C_{60}$ fullerene complex. The width of the inclusion complex produced was approximately 1 nm, and the height was approximately 2 nm.

(3) Preparation of the Electrode

On the other hand, an electrode 11 with anionic molecules on the surface was created by immersing a metal electrode in an ethanol solution containing sodium 2-mercaptoethane sulfonate.

(4) Fixing the Inclusion Complex

The inclusion complex is tightly arranged on the electrode by immersing the electrode prepared according to (3) above in an aqueous solution of inclusion complex (0.25 mmol/dm$^3$) in order to produce a biosensor. At this time, the inclusion complex was joined to the electrode by electrostatic interaction.

(5) Fixing the Polymer Film

The inclusion complex which was fixed on the electrode was immersed for 20 minutes at room temperature in a HEPES buffered solution (pH=7.0) containing PDDA (6 mg/ml), and a PDDA film was formed on the inclusion complex by electrostatic interaction. After washing in purified water, the electrode was immersed for 20 minutes at room temperature in a HEPES buffered solution (pH=7.0) containing PVS (4 mg/ml) to form a PVS layer on the PDDA layer by electrostatic interaction.

(6) Fixing the Receptor

Next, the electrode with the inclusion complex was immersed for 20 minutes at room temperature in a HEPES (2-[4-(2-hydroxyethyl)-1-piperazinyl]ethanesulfonic acid) buffered solution (pH=7.0) containing lactate dehydrogenase (0.2 mg/ml), and the enzyme was fixed on the inclusion complex by electrostatic interaction.

FOURTH EMBODIMENT

Figure 5:
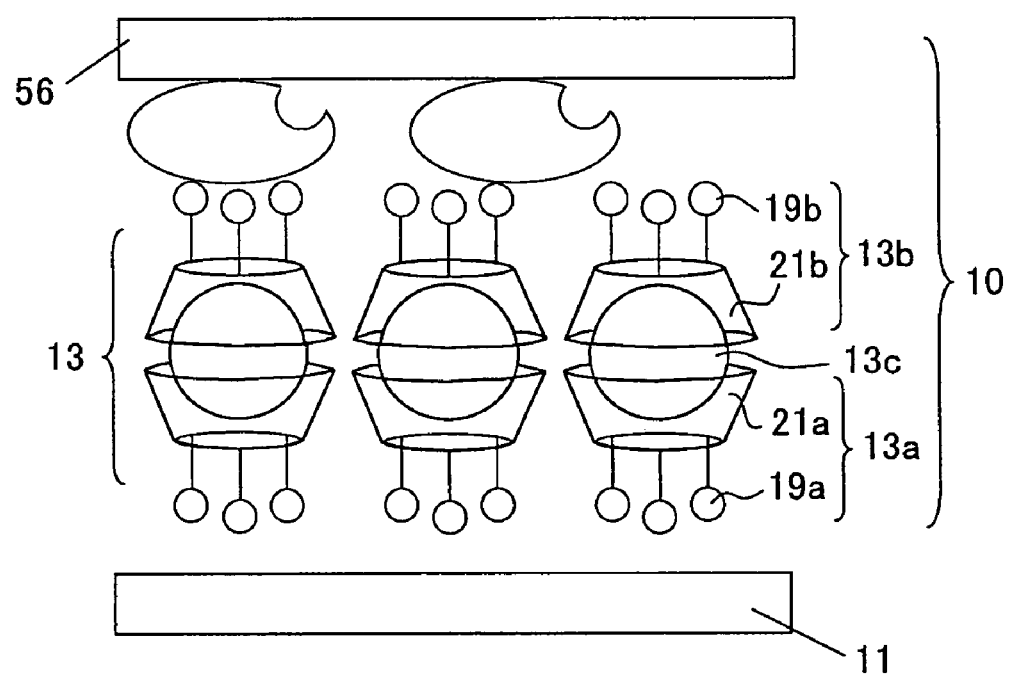
FIG. 5 shows the structure of the biosensor according to the fourth embodiment.

FIG. 5 shows the structure of the biosensor of the fourth embodiment. Flag numbers which are identical to those in FIG. 1 identify similar structural elements as those in the first embodiment. The biosensor of FIG. 5 comprises the target recognizing element 10 of FIG. 1 with a polyion complex film 56. The polyion complex film 56 is formed over the receptor 15, and strengthens the bond between the receptor 15 and the second host molecule 13b. Therefore, the durability of the biosensor can be increased. The polyion complex film 56 may be for instance a polyion complex film such as cationic poly-L-lysine or anionic glutamate or acrylate.

EXPERIMENTAL EXAMPLE 3

An experimental example in which an inclusion complex was created by including $C_{60}$ fullerene in calix[3]arene, and then lactate dehydrogenase as the receptor was fixed to the inclusion complex, is shown below.

(1) Synthesis of Calix[3]arene

First, using the triester derivatives of calix[3]arene as a raw material, an excess of N, N-dimethylpropane diamine was added to synthesize the precursor of the calix[3]arene using aminolysis. This precursor was N-methylated using dimethyl sulfate to synthesize calix[3]arene with quaternary amines on the end.

(2) Preparation of Calix[3]arene and $C_{60}$ Fullerene $C_{60}$ fullerene (72 mg, 0.1 mmol) was mixed into an aqueous solution of calix[3]arene (10 ml, 0.5 mmol/dm$^3$) synthesized as shown above, and after repeated agitation and ultrasonic treatment, the undissolved fullerene was removed by centrifugal separation, to prepare an aqueous solution of the inclusion complex which was the calix[3]arene and $C_{60}$ fullerene complex. The width of the inclusion complex produced was approximately 1 nm, and the height was approximately 2 nm.

(3) Preparation of the Electrode

On the other hand, an electrode 11 with anionic molecules on the surface was created by immersing a metal electrode in an ethanol solution containing sodium 2-mercaptoethane sulfonate.

(4) Fixing the Inclusion Complex

The inclusion complex is tightly arranged on the electrode by immersing the electrode prepared according to (3) above in an aqueous solution of inclusion complex (0.25 mmol/dm$^3$) in order to produce a biosensor. At this time, the inclusion complex was joined to the electrode by electrostatic interaction.

(5) Fixing the Receptor

Next, the electrode with the inclusion complex was immersed for 20 minutes at room temperature in a HEPES (2-[4-(2-hydroxyethyl)-1-piperazinyl]ethanesulfonic acid) buffered solution (pH=7.0) containing lactate dehydrogenase (0.2 mg/ml), and the enzyme was fixed on the inclusion complex by electrostatic interaction.

(6) Fixing the Polyion Complex Film

After fixing the enzyme to the inclusion complex, a polyion complex film is formed on the surface of the enzyme using a method of casting a 1 mM solution of poly-L-lysine.

INDUSTRIAL APPLICABILITY

Using the present invention, a target recognizing element can be provided wherein a receptor is fixed to an inclusion complex containing a mediator.

What is claimed is:

1. A target recognizing element comprising:
   a first calixarene molecule having a hydrophilic group and an inclusion site, wherein the hydrophillic group of the first calixarene molecule is bonded to an electrode;
   a second calixarene molecule having a hydrophilic group and an inclusion site;
   a receptor which is bonded to the hydrophilic group of the second calixarene molecule and a the target; and
   a fullerene molecule which is included in the inclusion site of the first calixarene molecule and in the inclusion site of the second calixarene molecule, and which transmits a charge produced by the reaction between the target and the receptor.

2. The target recognizing element according to claim 1, wherein the receptor is one or a combination of a plurality of substances selected from a group including enzymes, antibodies, DNA (deoxyribonucleic acid), and peptides.

3. The target recognizing element according to claim 1 further comprising at least one layer of a polymer film between the second calixarene molecule and the receptor.

4. The target recognizing element according to claim 3, wherein the polymer film is comprising a poly(diallyl dimethyl ammonium chloride) layer and a polyvinyl potassium sulfate layer.

5. The target recognizing element according to claim 1, further comprising a polyion complex film which covers the receptor.

6. The target recognizing element according to claim 1, wherein the receptor is bonded to the hydrophilic group of the second calixarene molecule under conditions in which the pH is between 4 and 8, and the temperature is between 15 and 45° C.

* * * * *